United States Patent
Webster-Smith et al.

(10) Patent No.: US 11,832,906 B2
(45) Date of Patent: Dec. 5, 2023

(54) CONTROLLING A SURGICAL INSTRUMENT

(71) Applicant: CMR SURGICAL LIMITED, Cambridge (GB)

(72) Inventors: David William Haydn Webster-Smith, Cambridge (GB); Luke David Ronald Hares, Cambridge (GB); Graham John Veitch, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 461 days.

(21) Appl. No.: 17/078,174

(22) Filed: Oct. 23, 2020

(65) Prior Publication Data
US 2021/0121254 A1   Apr. 29, 2021

(30) Foreign Application Priority Data
Oct. 28, 2019 (GB) ..................... 1915581

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/77* (2016.02); *B25J 9/1612* (2013.01); *B25J 15/0019* (2013.01)

(58) Field of Classification Search
CPC ......... A61B 34/35; A61B 34/77; A61B 34/70; A61B 34/74; A61B 34/30; A61B 18/1442
See application file for complete search history.

(56) References Cited

U.S. PATENT DOCUMENTS 6,491,701 B2 * 12/2002 Tierney .................. A61B 34/37
606/130
6,594,552 B1    7/2003 Nowlin et al.
(Continued)

FOREIGN PATENT DOCUMENTS

GB        2560384 A    9/2018
JP      2015506721 A    3/2015
(Continued)

OTHER PUBLICATIONS

United Kingdom Search Report from corresponding United Kingdom Application No. GB1915581.1 dated Apr. 8, 2020.
(Continued)

*Primary Examiner* — Julian W Woo
(74) *Attorney, Agent, or Firm* — Lando & Anastasi, LLP (57) ABSTRACT

A control system configured to control manipulation of a surgical instrument in response to manipulation of a remote surgeon input device, the surgical instrument comprising opposable first and second end effector elements connected to a shaft by an articulated coupling, the articulated coupling comprising a first joint driveable by a first pair of driving elements so as to permit the first end effector element to rotate, and a second joint driveable by a second pair of driving elements so as to permit the second end effector element to rotate, the control system configured to: detect a change of configuration of the surgeon input device to a gripping configuration at time t; respond to the change of configuration of the surgeon input device to the gripping configuration by commanding gripping forces to be applied to the first and second pairs of driving elements, so as to cause the first and second end effector elements to rotate in opposing rotational directions towards each other with a gripping closing force to a closed configuration; and if the first and second end effector elements are still in the closed configuration at time t+T, commanding a reduction in the
(Continued)

force applied to the first and second pairs of driving elements, thereby causing the first and second end effector elements to subsequently be held in a further closed configuration with a reduced closing force.

21 Claims, 6 Drawing Sheets

(51) Int. Cl.
  *B25J 9/16* (2006.01)
  *B25J 15/00* (2006.01)

(56) References Cited

U.S. PATENT DOCUMENTS

| | | | |
|---|---|---|---|
| 6,879,880 B2 * | 4/2005 | Nowlin | A61B 34/70 318/568.22 |
| 9,085,083 B2 | 7/2015 | Nixon | |
| 9,872,737 B2 * | 1/2018 | Nixon | A61B 34/37 |
| 10,813,703 B2 * | 10/2020 | Swayze | A61B 18/14 |
| 2012/0071892 A1 | 3/2012 | Itkowitz et al. | |
| 2013/0103050 A1 | 4/2013 | Richmond et al. | |

FOREIGN PATENT DOCUMENTS

| | | |
|---|---|---|
| WO | 2013018933 A1 | 2/2013 |
| WO | 2016187006 A1 | 11/2016 |
| WO | 2018162921 A1 | 9/2018 |
| WO | WO-2019164995 A1 * | 8/2019 ........... A61B 18/085 |

OTHER PUBLICATIONS

Notification of Transmittal of the International Search Report and the Written Opinion of the International Searching Authority from corresponding PCT/GB/2020/052682 dated Jan. 25, 2021.

Japanese Notification of Resons for Refusal from corresponding Japanese Patent Application No. 2022-524994 dated Mar. 31, 2023.

* cited by examiner

CONTROLLING A SURGICAL INSTRUMENT

CROSS-REFERENCE TO RELATED APPLICATION

This application claims the benefit under 35 U.S.C. § 119 of United Kingdom Patent Application No. 1915581.1 filed on Oct. 28, 2019 which is hereby incorporated herein by reference in its entirety for all purposes.

BACKGROUND

Figure 1:
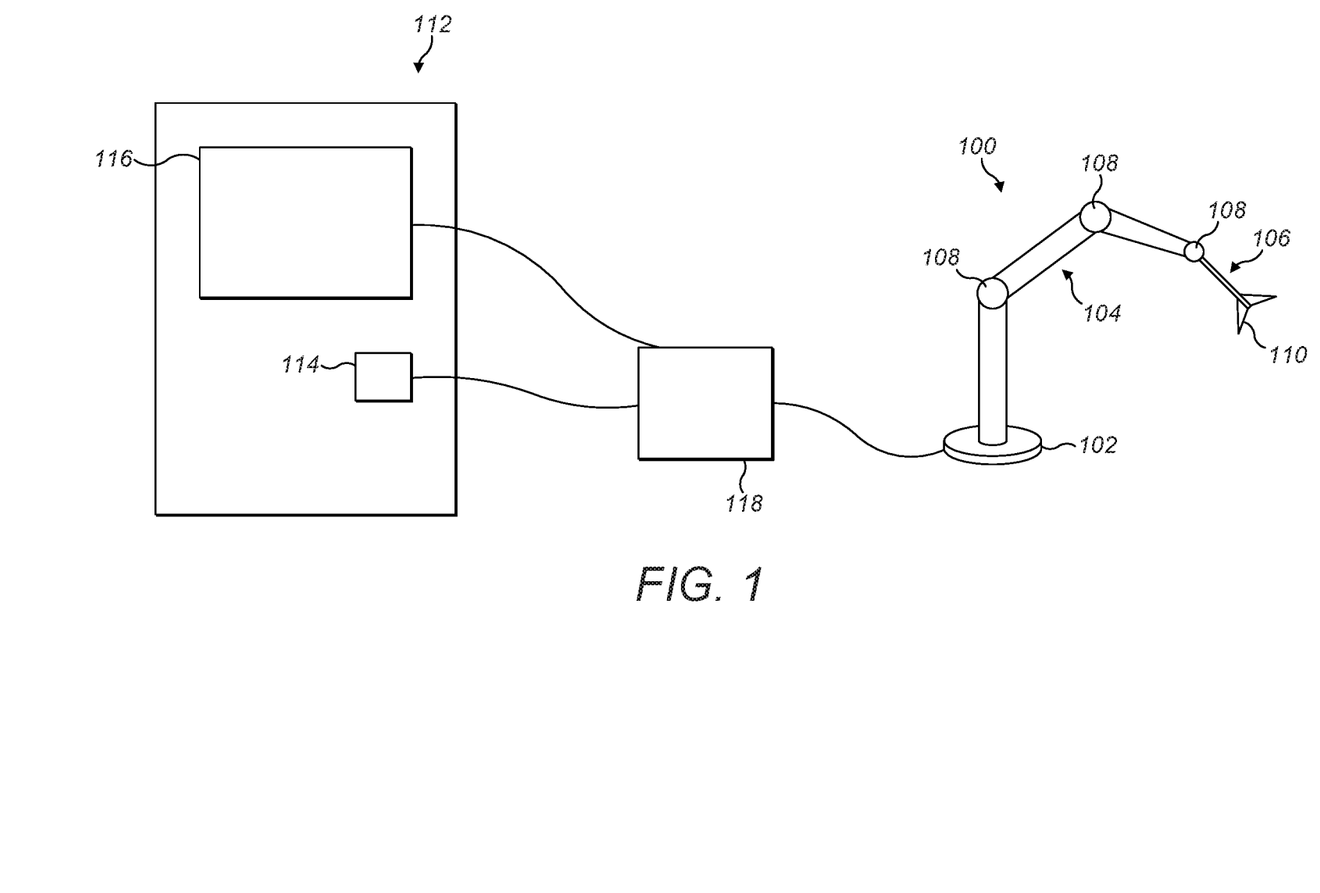
FIG. 1 illustrates a surgical robot system for performing a surgical procedure.

It is known to use robots for assisting and performing surgery. FIG. 1 illustrates a typical surgical robotic system. A surgical robot 100 consists of a base 102, an arm 104 and an instrument 106. The base supports the robot, and may itself be attached rigidly to, for example, the operating theatre floor, the operating theatre ceiling or a cart. The arm extends between the base and the instrument. The arm is articulated by means of multiple flexible joints 108 along its length, which are used to locate the surgical instrument in a desired location relative to the patient. The surgical instrument is attached to the distal end of the robot arm. The surgical instrument penetrates the body of the patient at a port so as to access the surgical site. At its distal end, the instrument comprises an end effector 110 for engaging in a surgical procedure. In FIG. 1, the illustrated end effector is a pair of jaws. A surgeon controls the surgical robot 100 via a remote surgeon console 112. The surgeon console comprises one or more surgeon input devices 114. These may take the form of a hand controller or foot pedal. The surgeon console also comprises a display 116.

A control system 118 connects the surgeon console 112 to the surgical robot 100. The control system receives inputs from the surgeon input device(s) and converts these to control signals to move the joints of the robot arm 104 and end effector 110. The control system sends these control signals to the robot, where the corresponding joints are driven accordingly.

Many end effectors comprise two end effector elements which are rotatable with respect to each other, such as the jaws shown in FIG. 1. It is known for these end effector elements to be individually driven by cables. These cables may be utilised to drive opening and closing of the end effector elements so as to grip and release an object between them, or cut through an object between them. To grip or cut an object, force is applied to the cables so as to cause the end effector elements to close together with force.

Surgeons prefer to maintain end effectors of this sort in a closed configuration when they are not utilising them. Maintaining an end effector in a closed configuration requires continual application of force to the cables driving its end effector elements. A surgeon may not use an instrument for a considerable time, for example up to 30 minutes. During the whole period of non-use, the motors driving the cables are generating a high torque, and hence dissipating significant heat.

The heat loss of the motors causes the robot arm to heat up. Safety regulations set maximum temperature limits of surfaces in the operating theatre which are allowed to be contacted by people. The maximum temperature limits depend on the length of time of the contact. For example, the current maximum temperature limit set by the medical electrical equipment and systems standard BS EN 60601 for a surface in the operating theatre which is able to be touched by an operator for up to 1 minute is 48° C.

It is known to utilise a cooling system to cool the robot arm down to meet the maximum temperature limits. However the cooling system adds additional complexity and weight to the robot arm, and can limit the maneuverability of the robot arm.

Thus, there is a need for a control system which reduces the heat loss generated by the motors in the robot arm so as to reduce the need for an arm cooling system.

SUMMARY OF THE INVENTION

According to an aspect of the invention, there is provided a control system for controlling manipulation of a surgical instrument in response to manipulation of a remote surgeon input device, the surgical instrument comprising opposable first and second end effector elements connected to a shaft by an articulated coupling, the articulated coupling comprising a first joint driveable by a first pair of driving elements so as to permit the first end effector element to rotate, and a second joint driveable by a second pair of driving elements so as to permit the second end effector element to rotate, the control system configured to: detect a change of configuration of the surgeon input device to a gripping configuration at time t; respond to the change of configuration of the surgeon input device to the gripping configuration by commanding gripping forces to be applied to the first and second pairs of driving elements, so as to cause the first and second end effector elements to rotate in opposing rotational directions towards each other with a gripping closing force to a closed configuration; and if the first and second end effector elements are still in the closed configuration at time t+T, commanding a reduction in the force applied to the first and second pairs of driving elements, thereby causing the first and second end effector elements to subsequently be held in a further closed configuration with a reduced closing force.

The control system may be configured to command the reduction in force to be applied gradually over a time $\Delta T$.

The control system may be configured to: detect a command from the surgeon input device to disengage active control of the surgical instrument by the surgeon input device; and in response to the detected command: disengage active control of the surgical instrument by the surgeon input device, and maintain the first and second end effector elements of the surgical instrument in the further closed configuration with the reduced closing force.

The control system may be configured to: detect a command at time T' from a surgeon input device to engage active control of the surgical instrument by the surgeon input device; and in response to the detected command: engage active control of the surgical instrument by the surgeon input device, and command gripping forces to be applied to the first and second pairs of driving elements, so as to cause the first and second end effector elements to be forced in opposing rotational directions towards each other with a gripping closing force.

The command detected at time T' may be from the same surgeon input device that disengaged active control of the surgical instrument and engaged active control of the further surgical instrument.

The command detected at time T' may be from a different surgeon input device to the surgeon input device that disengaged active control of the surgical instrument and engaged active control of the further surgical instrument.

The control system may be configured to, on detecting activity of the surgeon input device at time T', command gripping forces to be applied to the first and second pairs of driving elements, so as to cause the first and second end effector elements to be forced in opposing rotational directions towards each other with a gripping closing force.

The detected activity of the surgeon input device at time T' may be a movement of the user indicative of the user's presence or focus of attention on the surgical instrument.

The detected activity of the surgeon input device at time T' may be a rotation or translation of the surgeon input device in its workspace, or a detection of a user's hand in contact with the surgeon input device.

The detected activity of the surgeon input device at time T' may be an actuation of an input on the surgeon input device.

The control system may be configured to command forces to be applied to the first and second pairs of driving elements instantaneously.

The opposable first and second end effector elements may be a pair of scissors. In this case, T may be within the bounds: 1 second<T<10 seconds.

The control system may be configured to command the forces to be applied to the first and second pairs of driving elements gradually over a time ΔT'.

The opposable first and second end effector elements may be a needle driver. In this case, T may be within the bounds: 30 seconds<T<3 minutes.

The surgeon input device may comprise a body and a trigger, and be in a gripping configuration when the trigger has a position relative to the body that is within a specified range.

The gripping configuration of the surgeon input device may comprise a rotational position of the trigger relative to the body that is within a specified range of rotational positions.

The gripping configuration of the surgeon input device may comprise a linear position of the trigger relative to the body that is within a specified range of linear positions.

The control system may be configured to command gripping forces to be applied to the first and second pairs of driving elements by: applying a first gripping force to a first driving element of the first pair of driving elements, and applying a second gripping force to a second driving element of the second pair of driving elements, wherein the magnitudes of the first and second gripping forces are the same.

The control system may be configured to command a reduction in the force applied to the first and second pairs of driving elements by a function dependent on instrument type.

The gripping forces may be maximum forces.

The control system may be configured to continue to detect the gripping configuration of the surgeon input device for the time T.

BRIEF DESCRIPTION OF THE FIGURES

The present invention will now be described by way of example with reference to the accompanying drawings. In the drawings.

DETAILED DESCRIPTION

The following describes controlling a surgical robotic instrument from a remote surgeon console. The instrument and console form part of a surgical robotic system of the type illustrated in FIG. 1.

The surgical instrument is supported by a robot arm. The robot arm is itself supported by a base. During surgery, the base is secured to part of the operating theatre, for example the floor, ceiling, cart or patient bed. The robot arm remains at all times external to the patient. The robot arm comprises a series of arm links interspersed with joints. These joints may be revolute joints. The end of the robot arm distal to the base can be articulated relative to the base by movement of one or more of the joints. The surgical instrument attaches to a drive assembly at the distal end of the robot arm. This attachment point is external to the patient.

The surgical instrument has an elongate profile, with a shaft spanning between its proximal end which attaches to the robot arm and its distal end which accesses the surgical site within the patient body. The proximal end of the surgical instrument and the instrument shaft may be rigid with respect to each other and rigid with respect to the distal end of the robot arm when attached to it. An incision is made into the patient body, through which a port is inserted. The surgical instrument may penetrate the patient body through the port to access the surgical site. Alternatively, the surgical instrument may penetrate the body through a natural orifice of the body to access the surgical site. At the proximal end of the instrument, the shaft is connected to an instrument interface. The instrument interface engages with the drive assembly at the distal end of the robot arm. Specifically, individual instrument interface elements of the instrument interface engage individual drive assembly interface elements of the drive assembly. The instrument interface is releasably engageable with the drive assembly. The instrument can be detached from the robot arm manually without requiring any tools. This enables the instrument to be detached from the drive assembly quickly and another instrument attached during an operation.

Figure 2:
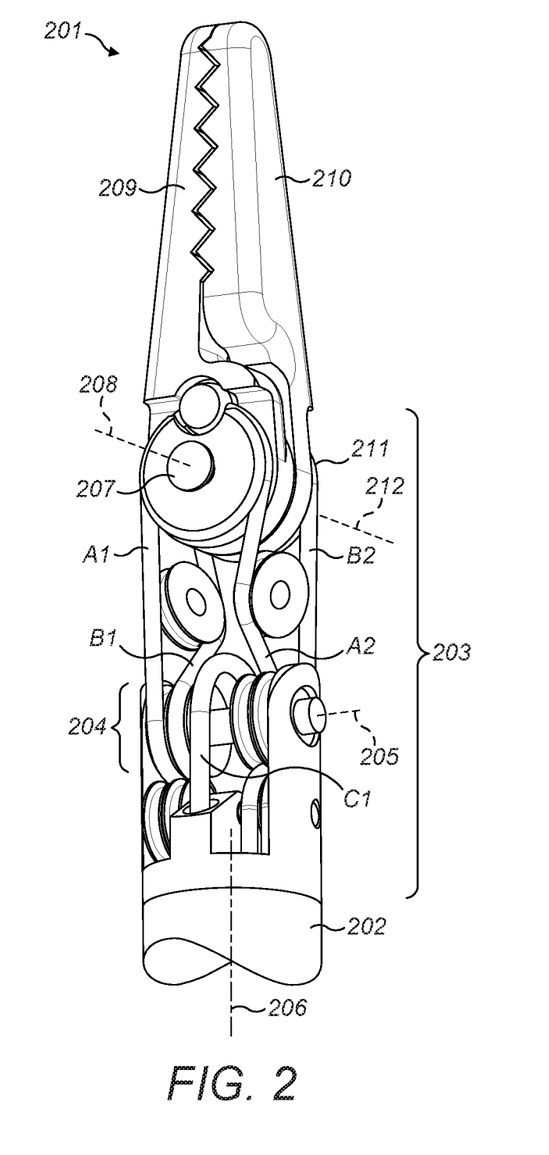
FIG. 2 illustrates the distal end of an exemplary surgical instrument.

At the distal end of the surgical instrument, the shaft is connected to an end effector by an articulated coupling. The end effector engages in a surgical procedure at the surgical site. FIG. 2 illustrates the distal end of an exemplary instrument which has a pair of jaws as the end effector 201. The shaft 202 is connected to the end effector 201 by articulated coupling 203. The articulated coupling 203 comprises several joints. These joints enable the pose of the end effector to be altered relative to the direction of the instrument shaft. The end effector may also comprise joint(s). In the example of FIG. 2, the articulated coupling 203 comprises a pitch joint 204. The pitch joint 204 rotates about pitch axis 205, which is perpendicular to the longitudinal axis 206 of the shaft 202. The pitch joint 204 permits a supporting body (described below) and hence the end effector to rotate about the pitch axis 205 relative to the shaft. In the example of FIG. 2, the end effector comprises a first yaw joint 207 and a second yaw joint 211. First yaw joint 207 rotates about first yaw axis 208. Second yaw joint 211 rotates about second yaw axis 212. Both yaw axes 208 and 212 are perpendicular to pitch axis 205. Yaw axes 208 and 212 may be parallel. Yaw axes 208 and 212 may be collinear.

The articulated coupling 203 comprises a supporting body. At one end, the supporting body is connected to the shaft 202 by pitch joint 204. At its other end, the supporting body is connected to the end effector 201 by the yaw joints 207 and 211. This supporting body is omitted from FIG. 2 for ease of illustration so as to enable the other structure of the articulated coupling to be more easily seen.

The end effector comprises two end effector elements 209, 210. The end effector elements shown are opposing jaws. However, the end effector elements may be any type of opposing end effector elements, further examples of which are discussed later. The first yaw joint 207 is fast with the first end effector element 209 and permits the first end effector element 209 to rotate about the first yaw axis 208 relative to the supporting body and the pitch joint 204. The second yaw joint 211 is fast with the second end effector element 210 and permits the second end effector element 210 to rotate about the second yaw axis 212 relative to the supporting body and the pitch joint 204.

The joints illustrated in FIG. 2 are driven by pairs of driving elements. The driving elements are elongate. They are flexible transverse to their longitudinal extent. They resist compression and tension forces along their longitudinal extent. Each pair of driving elements is secured at the other end of the instrument shaft to a respective instrument interface element of the instrument interface. Thus, the robot arm transfers drive to the end effector as follows: movement of a drive assembly interface element moves an instrument interface element which moves a driving element which moves one or more joint of the articulation and/or end effector which moves the end effector. The driving elements may be cables. The driving elements may comprise flexible portions and a rigid portion. Flexible portions engage the components of the instrument interface and the articulated coupling, and the rigid portion extends through all or part of the instrument shaft. For example, the flexible portion may be a cable, and the rigid portion may be a spoke. Other rigid portion(s) may be in the instrument interface or articulated coupling of the instrument. For example, rack and pinions may be in the instrument interface or articulated coupling of the instrument.

FIG. 2 illustrates a first pair of driving elements A1, A2 which are constrained to move around the first yaw joint 207. Driving elements A1, A2 drive rotation of the first end effector element 209 about the first yaw axis 208. FIG. 2 illustrates a second pair of driving elements B1, B2 which are constrained to move around the second yaw joint 211. Driving elements B1, B2 drive rotation of the second end effector element 210 about the second yaw axis 212.

FIG. 2 also illustrates a third pair of driving elements C1, C2 which are constrained to move around pitch joint 204. Driving elements C1, C2 drive rotation of the end effector 201 about the pitch axis 205. The pitch joint 204 and yaw joints 207, 211 are independently driven by their respective driving elements.

The end effector elements 209 and 210 are independently rotatable. The end effector elements can be rotated in opposing rotational directions. For example, the end effector elements can be rotated in opposing rotational directions towards each other by applying tension to driving elements A2 and B1. This closes the end effector elements together, which is useful for (i) gripping an object between the end effector elements, such as tissue or a needle or thread, and/or (ii) cutting an object between the end effector elements, such as tissue or thread. The end effector elements can be rotated in opposing rotational directions away from each other by applying tension to driving elements A1 and B2. This opens the end effector elements, which is useful for (i) releasing an object which has been grasped between the end effector elements, and/or (ii) reopening a pair of scissor end effector elements ready for another cutting action. Both end effector elements can be rotated in the same rotational direction, by applying tension to driving elements A1 and B1 or alternatively A2 and B2. This causes the end effector elements to yaw about the pivot axes 208 and 212. This is useful for enabling the end effector to access a different part of the surgical site. Alternatively, one end effector element can be rotated (in either rotational direction) whilst the other end effector element is maintained in position, by applying tension to only one of driving elements A1, A2, B1, B2. Thus, both a gripping motion and a yawing motion of the end effector is enabled by manipulating the same pairs of driving elements: A1, A2 for the first end effector element 209, and B1, B2 for the second end effector element 210.

There are at least two types of instruments having opposable end effectors which are relevant to the following description. The first type is cutting instruments, for which the end effector elements engage so as to cut tissue or another object between the end effector elements. The second type is gripping instruments, for which the end effector elements engage so as to grasp tissue or another object between the end effector elements.

The surgeon console comprises one or more surgeon input devices. Each surgeon input device enables the surgeon to provide a control input to the control system. A surgeon input device may, for example, be a hand controller, a foot controller such as a pedal, a touch sensitive input to be controlled by a finger or another part of the body, a voice control input device, an eye control input device or a gesture control input device. The surgeon input device may provide several inputs which the surgeon can individually operate.

Figure 3:
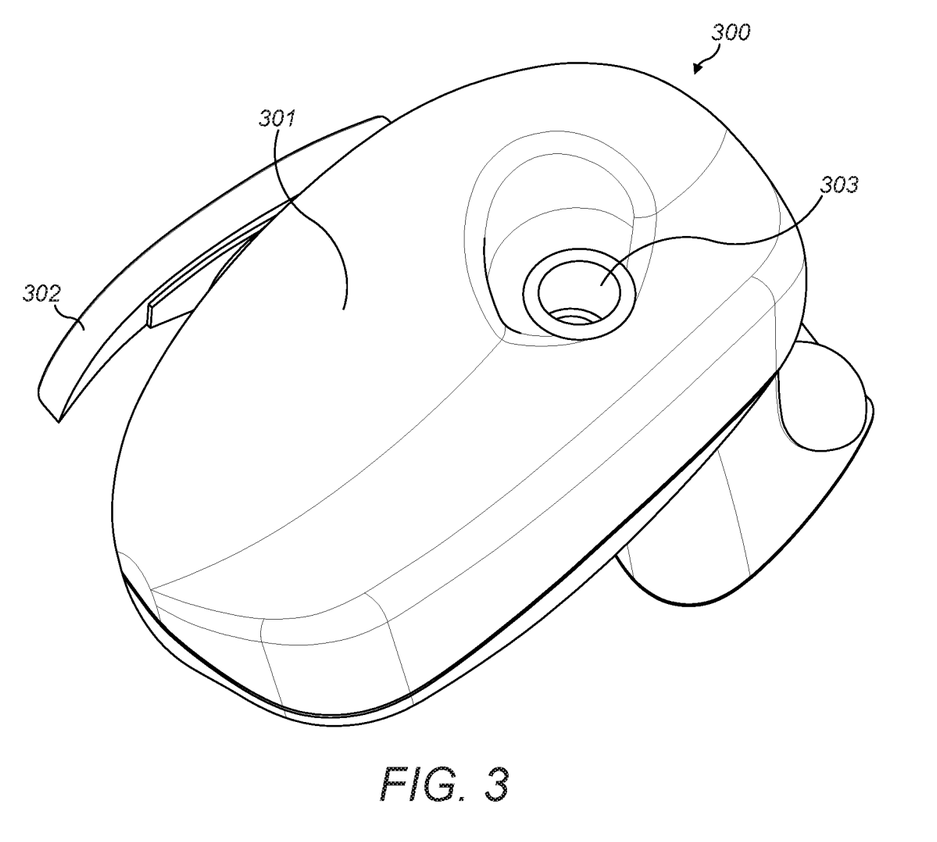
FIG. 3 illustrates an exemplary surgeon input device.

FIG. 3 illustrates an exemplary hand controller 300. The hand controller is connected to the surgeon console, for example by a gimbal arrangement (not shown). This enables the hand controller to be moved with three degrees of translational freedom with respect to the surgeon console. The hand controller shown is intended to be held by a right hand. A mirror image hand controller could be held by a left hand. The hand controller comprises a body 301 suitable for being gripped by a hand. The hand controller may comprise additional inputs, for example buttons, switches, levers, slide inputs or capacitive sensor inputs such as track pads 303. The hand controller of FIG. 3 comprises a trigger 302. The trigger 302 is movable relative to the body 301. In the hand controller shown, the trigger 302 is rotatable relative to the body 301. Alternatively, or in addition, the trigger could translate linearly relative to the body 301. The hand controller may comprise two triggers, each trigger for independently controlling a single different one of the end effector elements 209, 210.

The surgeon may rotate the trigger 302 relative to the body 301 of the hand controller in order to command the end effector elements 209, 210 of the instrument to close in a gripping/closing motion or to open in a releasing/opening motion. For example, the surgeon may rotate the trigger 302 towards the body 301 of the hand controller to command a gripping motion. The surgeon may rotate the trigger 302 away from the body 301 of the hand controller to command a releasing motion. The surgeon may rotate the body of the hand controller in the hand controller workspace to command a change in orientation of the end effector elements.

A control system connects the surgeon console to the surgical robot. The control system comprises a processor and a memory. The memory stores, in a non-transient way, software code that can be executed by the processor to cause the processor to control the surgeon console and robot arm and instrument in the manner described herein. The control system receives the inputs from the surgeon input device(s) and converts these to control signals to move the joints of the robot arm and/or the joint(s) of the articulated coupling and/or the joint(s) of the end effector. The control system sends these control signals to the robot arm, where the corresponding joints are driven accordingly. Manipulation of the surgical instrument is thereby controlled by the control system in response to manipulation of the surgeon input device.

When the control system is controlling an instrument, on detecting that the hand controller is in a gripping configuration, the control system responds by commanding a force to be applied to the driving elements of the end effector elements to cause the end effector elements to rotate in opposing rotational directions towards each other. Referring to FIG. 2, the control system responds to detecting the gripping configuration by commanding a force to be applied to A2 and B1, thereby causing the end effector elements to close together.

The gripping configuration of the hand controller is one in which the rotational position of the trigger relative to the body is within a specified range. The specified range may be predetermined. The specified range may be dependent on the instrument type. For the case that the trigger translates linearly relative to the body, the gripping configuration of the hand controller is one in which the linear position of the trigger relative to the body is within a specified range. The specified range may be dependent on the instrument type. The specified range may be predetermined.

For a gripping action, a high gripping force of the end effector elements may be desirable. For example, if the end effector is a needle driver, then a high gripping force is desirable to enable holding a needle firmly whilst driving into tissue. As another example, if the end effector is a pair of scissors, then a high closing force is desirable to enable successful cutting of tissue. Thus, the control system responds to detecting a gripping configuration of the hand controller by commanding a gripping force to be applied to the driving elements so as to cause a gripping closing force of the end effector elements. Referring to FIG. 2, the control system responds by commanding a gripping force to be applied to A2 and a gripping force to be applied to B1. This results in the end effector elements 209 and 210 rotating towards each other with a gripping closing force, and thereby enabling the end effector to grip/cut with a gripping force. The gripping closing force continues to be applied after the end effector elements 209 and 210 have contacted each other (or each contacted an object held between them) in a closed configuration. The continued application of the gripping closing force causes the end effector elements 209 and 210 to push against each other (or the object held between them). This continued application of the gripping closing force is known as overgripping or overclosing. The gripping force applied to the driving elements may be the maximum force that can be applied to those driving elements. In this case, the subsequent closing force of the end effector elements is then the maximum force with which those end effector elements can be closed.

If the driving elements are driven in tension, as in the example of FIG. 2, then the maximum forces applied to the driving elements are tension forces. Each maximum force is the maximum tension force that can be applied to that driving element without it failing, for example by stretching or snapping. If the driving elements are driven in compression, then the maximum force applied to the driving elements are compression forces. Each maximum force is the maximum compression force that can be applied to that driving element without it failing, for example by compressing or fracturing. If the driving elements are driven in both tension and compression, for example if they are push rods, then a maximum tension force and a maximum compression force are defined. The maximum tension force is the maximum force that can be applied to the driving element in tension without it failing. The maximum compression force is the maximum force that can be applied to the driving element in compression without it failing. If the driving elements are driven in torsion, for example if they are lead screws, then the maximum force applied to the driving elements are torsional forces. Each maximum force is the maximum torsional force that can be applied to that driving element without it failing.

The control system commands a first gripping force to be applied to the driving element driving rotation of the first end effector element towards the second end effector element. In the example of FIG. 2, the control system commands a first gripping force to be applied to A2 to drive end effector element 209 to rotate towards end effector element 210. This may be a first maximum force. The control system commands a second gripping force to be applied to the driving element driving rotation of the second end effector element towards the first end effector element. In the example of FIG. 2, the control system commands a second gripping force to be applied to B1 to drive end effector element 210 to rotate towards end effector element 209. This may be a second maximum force.

The value of the first gripping force and the value of the second gripping force may be dependent on the instrument type. The first gripping force and the second gripping force may be the same. For example, if the end effector elements match, and the driving elements which drive each of those end effector elements match, as in the example of FIG. 2, then for a configuration in which the end effector elements are not fully closed and exerting forces against each other, the control system may command the same gripping force to be applied to both the first driving element A2 and the second driving element B1. Alternatively, the first gripping force and the second gripping force may be different. For example, if the end effector elements are different, then the first gripping driving force applied to the first end effector element may be different to the second gripping driving force applied to the second end effector element in order to achieve the desired gripping closing force of the end effector elements. An example of this would be an asymmetric instrument such as a stapler.

For gripping instruments, the gripping closing force is sufficient to enable gripping of an object between the first and second end effector elements. This gripping may be under resistive force, for example a needle driver gripping a needle whilst driving the needle firmly into tissue. For example, the gripping closing force may be in the range 10-15 N. For cutting instruments, the gripping closing force is sufficient to enable cutting of an object (typically tissue) between the first and second end effector elements. For example, the gripping closing force may be in the range 5-10 N.

Maintaining an instrument in a closed configuration in which the end effector elements press against each other with the gripping closing force, requires the motors driving that motion to generate a high torque, which causes significant heat loss.

Figure 4:
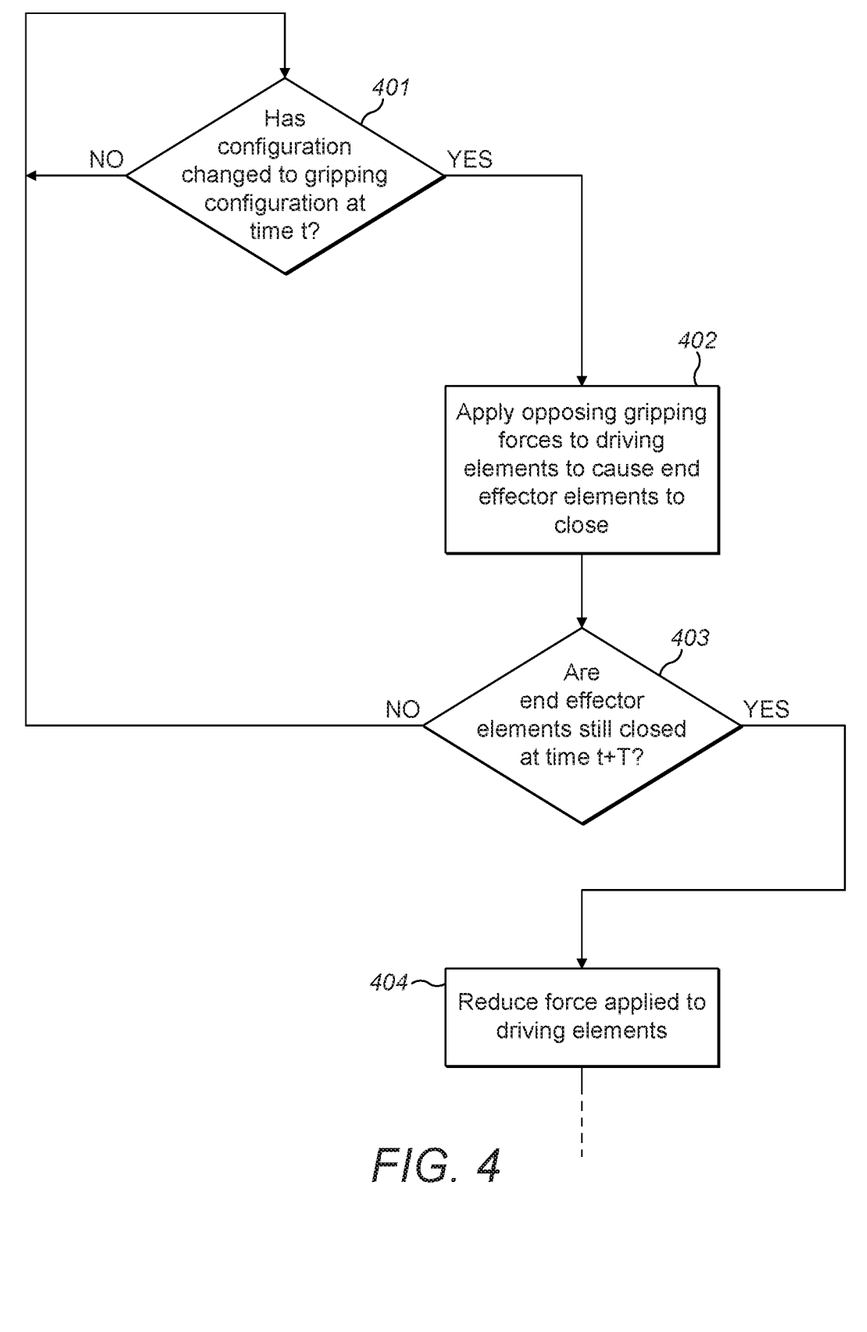
FIG. 4 is a flowchart of a method of controlling manipulation of a surgical instrument.

FIG. 4 illustrates a method implemented by the control system to reduce the heat loss generated by the motors.

At step 401, the control system detects whether the configuration of the surgeon input device has changed to a gripping configuration. The hand controller 300 may include a position sensor which senses the rotational (or linear) position of the trigger 302 relative to the body 301 of the hand controller. The control system receives the sensed rotational (or linear) position of the trigger from the position sensor. The control system determines that the configuration has changed to a gripping configuration if the received sensed rotational (or linear) position of the trigger is within the specified range for the gripping configuration for that instrument type. The control system determines that the configuration has not changed to a gripping configuration if the received sensed rotational (or linear) position of the trigger is not within the specified range for the gripping configuration for that instrument type.

If at step 401, the control system detects that the configuration of the surgeon input device has not changed to a gripping configuration, then the control system returns to step 401. The control system may wait for a time interval $T^1$ before repeating step 401.

If at step 401, the control system detects that the configuration of the surgeon input device has changed to a gripping configuration, then the control system moves to step 402. The time at which the change to the gripping configuration is detected is taken as time t. At step 402, the control system commands opposing gripping forces to be applied to the driving elements of the end effector elements, so as to cause the end effectors to close with a gripping closing force to a closed configuration. In the example of FIG. 2, this would be applying gripping driving forces to A2 and B1. The closed configuration is one in which either (i) the end effector elements are in contact (as is the case for a pair of scissors), or (ii) the end effector elements are both in contact with an object which is held between them (as is the case for a pair of jaws holding an object such as tissue). The closed configuration is an overgripping configuration. In other words, the end effector elements are pressing against each other (or the object between them) with a greater force than is required to maintain their relative positions.

Following step 402, the control system moves to step 403. At step 403, the control system detects if the first and second end effector elements are still in the closed configuration at a time t+T. The instrument may have been under the active control of the surgeon input device for the time T. In other words, the instrument is "engaged" for the time T. In this case, the control system would have continued to detect the gripping configuration of the surgeon input device for the time T. Alternatively, the instrument may have stopped being under the active control of the surgeon input device at some time between t and t+T. In other words, the instrument is "disengaged". In this case, the control system would have discontinued detecting the gripping configuration of the surgeon input device at some time between t and t+T.

The time T is dependent on instrument type. In the example that the instrument is a pair of scissors: T may be in the range 1 second<T<30 seconds, or 10 seconds<T<20 seconds for an engaged instrument, and 1 second<T<10 seconds, or 4 seconds<T<6 seconds for a disengaged instrument. T may be 5 seconds. In the example that the instrument is a needle driver: T may be in the range 1 minute<T<8 minutes, or 4 minutes<T<5 minutes for an engaged instrument, and 30 seconds<T<3 minutes, or 40 seconds<T<90 seconds for a disengaged instrument. T may be 60 seconds. T may also be dependent on other factors. For example T may be dependent on one or more of: the surgical operation being performed; the stage of the operation; the total running time of the system/motors of interest; the total overgripping time, optionally weighted by the overgripping force; whether the instrument is engaged or disengaged from the surgeon input device; risk factors specific to the operation, such as whether the needle holder is holding tissue or a needle; the operation mode of the system; whether the instrument is in the field of vision or not; and the temperature of the joints of the robot arm holding the instrument.

If at step 403, the control system detects that the first and second end effector elements are still in the closed configuration, then the control system returns to step 401. For example, before time T has passed, the surgeon may resume manipulation of the instrument, for example by opening the jaws of a pair of scissors following a cutting action.

If at step 403, the control system detects that the first and second end effector elements are still in the closed configuration at time t+T, then it moves to step 404. At step 404, the control system commands a reduced force to be applied to the driving elements which are causing the end effector elements to close. In the example of FIG. 2, this would be reducing the driving forces applied to A2 and B1.

The factor by which the force is reduced to the driving elements may be dependent on the instrument type. The force reduction value may be solely dependent on instrument type. The force reduction value for each instrument type may be empirically determined. Examples of instrument types for which the force reduction value may be solely dependent on instrument type are jaws and fenestrated graspers.

By reducing the force applied to the driving elements, the end effector elements are held in a further closed configuration, with a reduced closing force. This reduces the torques that the motors driving the driving elements are required to generate, and hence reduces the power dissipated as heat by those motors.

The further closed configuration of the end effector elements is suitably not an overgripping configuration. In other words, the force applied to the driving elements at step 404 is reduced so as to no longer apply additional force to the end effector elements beyond that required to hold the end effector elements in a closed configuration in which either (i) the end effector elements are in contact (as is the case for a pair of scissors), or (ii) the end effector elements are both in contact with an object which is held between them (as is the case for a pair of jaws holding an object such as tissue). If the end effector elements maintain their position in the absence of force applied to them, then suitably the reduced closing force is zero.

The reduction in force at step 404 may be applied gradually over a time ΔT. For an engaged instrument, 10 ms<ΔT<500 ms. ΔT may be 100 ms. For a disengaged instrument, 1 s<ΔT<5 s. ΔT may be 2 seconds. The reduction in force may be applied linearly over time. This helps to prevent jerky movement of the end effector elements caused by a sudden change in applied force. Alternatively, the reduction in force at step 404 may be instantaneous.

Optionally, the control system may only apply the reduction in force at step 404 if, in additional to detecting that the end effector elements are still in the closed configuration at time t+T, the control system also detects that the surgeon has disengaged active control of the surgical instrument by the surgeon input device.

Figure 5:
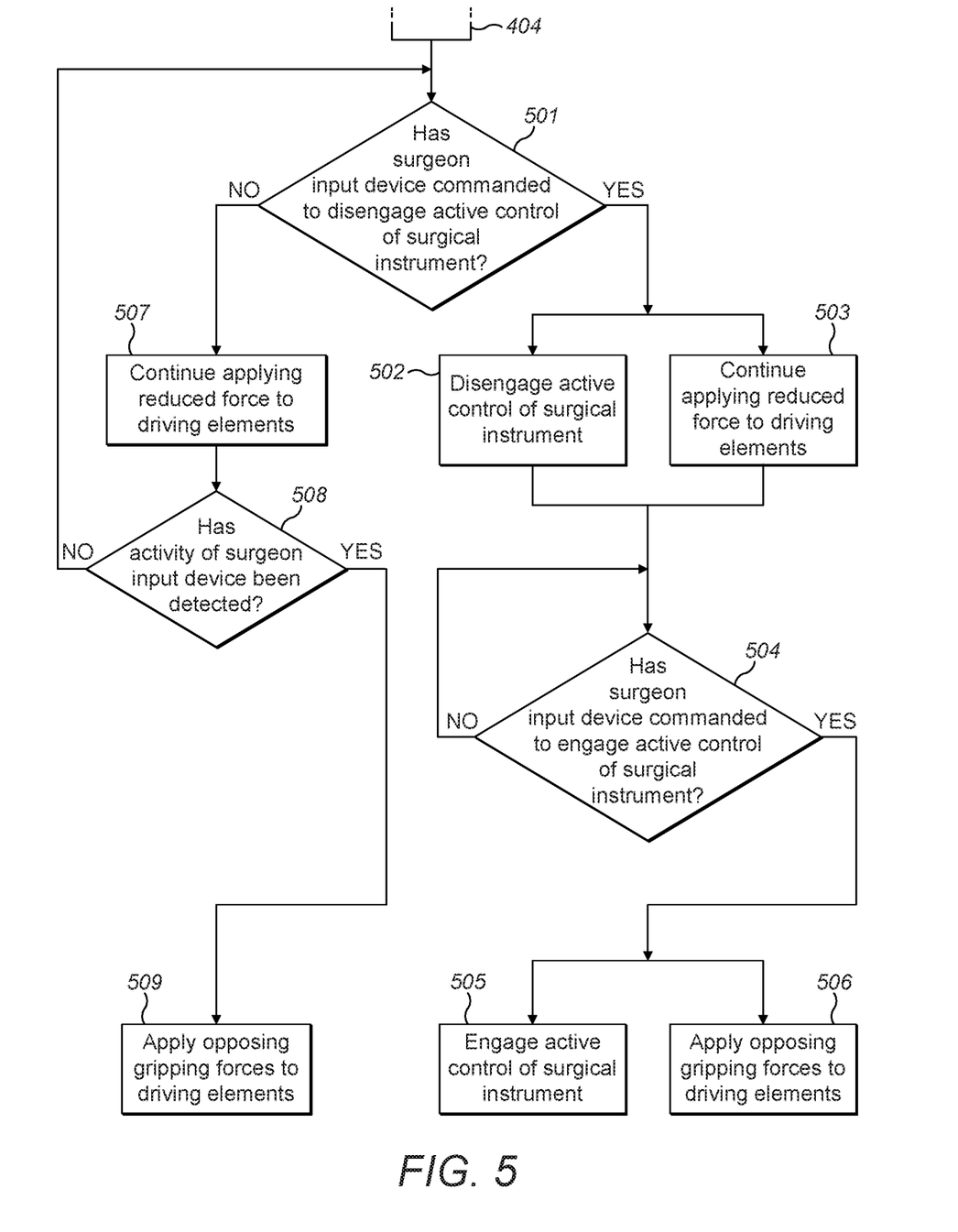
FIG. 5 is a flowchart of a further method of controlling manipulation of a surgical instrument.

FIG. 5 illustrates an additional method which may be implemented by the control system when the reduced force has been applied to the driving elements at step 404 of FIG. 4.

Step 501 follows on from step 404 of FIG. 4. At step 501, the control system determines whether the surgeon input device or, more generally, the surgeon console, has commanded active control of the surgical instrument by the surgeon input device to be disengaged. An input on the surgeon input device, for example a button, may be actuated to select an option from a menu displayed on the monitor of the surgeon console monitor. One of the options on the menu may be to disengage active control of the surgical instrument by the surgeon input device. Active control of the surgical instrument by the surgeon input device may be disengaged as a result of the surgeon input device no longer detecting the presence of the user's hand on the surgeon input device. Active control of the surgical instrument by the surgeon input device may be disengaged as a result of the surgeon console detecting that the user is either not present or not engaged in the operation of the surgical instrument. For example, a movement tracker may be used to track the user's body movements in order to to detect the user's presence and/or focus of attention. For example, the movement tracker may track the user's head and/or eye movement. From this, the control system deduces whether the user is present and/or paying attention. On detecting that the user is either not present, or not paying attention to a surgical instrument, active control of that surgical instrument by the surgeon input device may be disengaged. The detector for detecting the user's presence and/or focus of attention may be located: on the support structure of the surgeon console, on the display of the surgeon console, or on the surgeon input device itself. Optionally, the control system may additionally determine that the surgeon input device has commanded engagement of active control of another surgical instrument.

If the answer to step 501 is yes, then the control system moves to steps 502 and 503 which are implemented in parallel. At step 502, the control system disengages active control of the surgical instrument from the surgeon input device. If the surgeon input device has additionally commanded engagement of active control of another surgical instrument, then the control system engages active control of that other surgical instrument by the surgeon input device.

At step 503, the control system continues to maintain the first and second end effector elements of the surgical instrument in the further closed configuration by commanding the reduced closing forces to continue to be applied. These reduced closing forces have been applied continually since step 404 of FIG. 4.

The control system then moves to step 504. At step 504, the control system determines whether a surgeon input device has commanded active control of the surgical instrument to be engaged. This command may come from the same surgeon input device that commanded active control of the surgical instrument to be disengaged at step 501. Alternatively, this command may come from another surgeon input device. For example, a surgeon may control two hand controllers of the type illustrated in FIG. 3: one controlled by his left hand, and the other controlled by his right hand. The surgeon may have disengaged control of an instrument by his left hand controller, and subsequently engage control of that same instrument by his right hand controller.

If at step 504, the control system determines that a surgeon input device has not commanded to engage active control of the surgical instrument, then the control system returns to step 504. The control system may wait for a time interval $T^2$ before repeating step 504.

If at step 504, the control system determines that a surgeon input device has commanded to engage active control of the surgical instrument, then the control system moves to steps 505 and 506 which are implemented in parallel. The time at which the surgeon input device commands control of the surgical instrument to be engaged by it is taken as time T'.

At step 505, the control system engages active control of the surgical instrument by the surgeon input device that commanded it at step 504.

At step 506, the control system commands opposing gripping forces to be applied to the driving elements of the end effector elements, so as to cause the end effectors to close with a gripping closing force. In the example of FIG. 2, this would be applying gripping driving forces to A2 and B1. Suitably, the same opposing gripping forces are applied at step 506 as were applied at step 402.

If at step 501, the control system continues to maintain the first and second end effector elements of the surgical instrument in the further closed configuration by commanding the reduced closing forces to continue to be applied. These reduced closing forces have been applied continually since step 404 of FIG. 4.

The control system then moves on to step 508. At step 508, the control system determines whether any activity of the surgeon input device has been detected. Detected activity may, for example, be a movement of the surgeon input device in its workspace. For example, a rotation or translation of the surgeon input device. Detected activity may, for example, be an actuation of an input on the surgeon input device. For example pressing a button, switching a switch, moving a joystick, moving a trackpad or tracking ball, or sliding a slider.

If, at step 508, no activity of the surgeon input device has been detected, then the control system returns to step 501. The control system may wait for a time interval $T^3$ before repeating step 501.

If, at step 508 the control system determines that activity of the surgeon input device has been detected, then the control system moves to step 509. At step 509, the control system commands opposing gripping forces to be applied to the driving elements of the end effector elements, so as to cause the end effectors to close with a gripping closing force. In the example of FIG. 2, this would be applying gripping driving forces to A2 and B1. Suitably, the same opposing gripping forces are applied at step 509 as were applied at step 403.

The increase in force at step 506 or 509 may be applied gradually over a time $\Delta T'$. $\Delta T'$ may depend on the overgripping force to be applied. 10 ms<$\Delta T'$<500 ms. $\Delta T'$ may be 100 ms. The increase in force may be applied linearly over time. This helps to prevent jerky movement of the end effector elements caused by a sudden change in applied force. Alternatively, the increase in force at step 506 or 509 may be instantaneous.

Following step 506 or 509, the control system returns to step 403 of FIG. 4. For the next iteration of the control loop, the time at which the opposing gripping forces were applied at step 506 or 509 is taken as time t.

Figure 6:
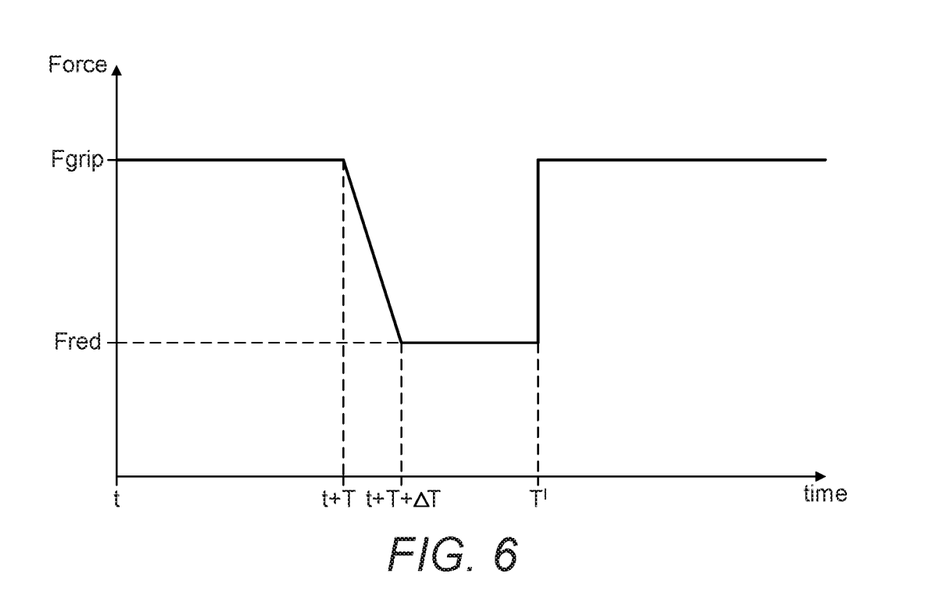
FIG. 6 is a graph illustrating a driving force applied over time to a pair of surgical scissors.

FIG. 6 is a graph illustrating the driving force applied over time to the driving elements of an exemplary pair of surgical scissors. At a time t, the gripping configuration is detected at step 401 of FIG. 4. Gripping forces Fgrip are applied to the driving elements. After a time T, the control system detects that the end effector elements are still in the closed configuration at step 403 of FIG. 4. A reduced force Fred is applied to the driving elements. The reduction from Fgrip to Fred occurs gradually over a time ΔT. That reduced force Fred is applied to the driving elements until a time T' when the control system either detects activity of the surgeon input device (at step 508 of FIG. 5) or that active control of the instrument has been engaged by a surgeon input device (at step 501 of FIG. 5). At time T', the gripping forces Fgrip are applied to the driving elements. This is done instantaneously. Alternatively, with a pair of scissors or another surgical instrument, on detecting activity of the surgeon input device or that active control of the instrument has been engaged by a surgeon input device, the control system may maintain application of the force Fred to the driving elements rather than increasing the force to Fgrip. When active control of a pair of scissors is engaged, the surgeon's next action with respect to the blades of the scissors is likely to be to open them for another cutting action. Thus, returning the closing force between the scissor blades to the gripping force by applying Fgrip to the driving elements may not be desirable.

Figure 7:
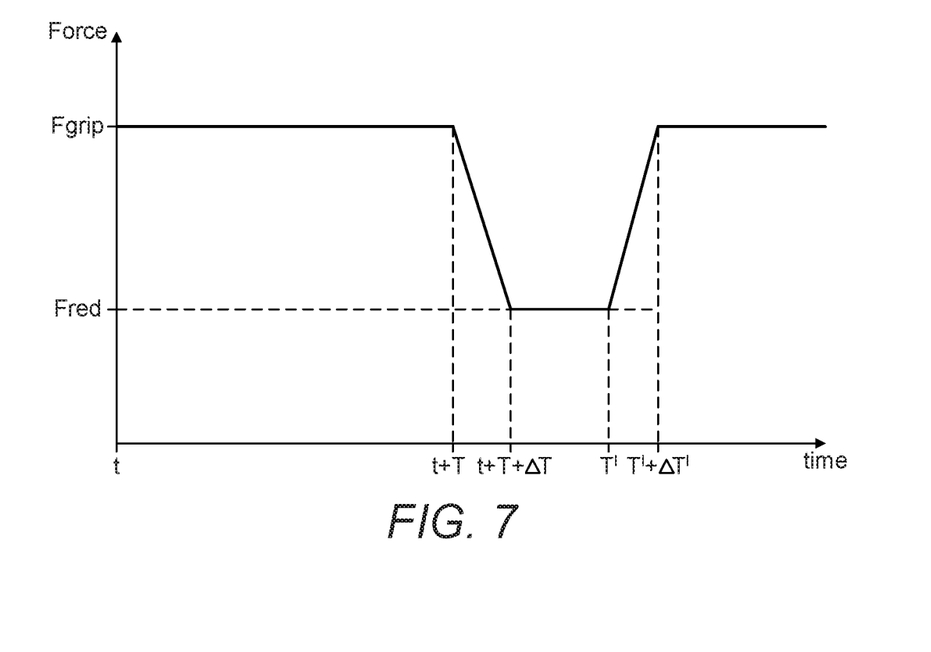
FIG. 7 is a graph illustrating a driving force applied over time to a surgical needle driver.

FIG. 7 is a graph illustrating the driving force applied over time to the driving elements of an exemplary needle driver. At a time t, the gripping configuration is detected at step 401 of FIG. 4. Gripping forces Fgrip are applied to the driving elements. After a time T, the control system detects that the end effector elements are still in the closed configuration at step 403 of FIG. 4. A reduced force Fred is applied to the driving elements. The reduction from Fgrip to Fred occurs gradually over a time ΔT. That reduced force Fred is applied to the driving elements until a time T' when the control system either detects activity of the surgeon input device or that active control of the instrument has been engaged by a surgeon input device. An increase in force to the gripping forces Fgrip are applied to the driving elements. The increase from Fred to Fgrip occurs gradually over a time ΔT'. When active control of a needle driver is engaged, the surgeon's next action with respect to the needle driver is likely to be to maintain grip of the needle and drive it into tissue. This action benefits from the needle driver gripping the needle with a high gripping force due to the resistive forces applied by the tissue on the needle. Thus, returning the closing force between the needle driver elements to the griping force by applying Fgrip is desirable.

The methods described herein reduce the heat loss generated by the motors by reducing the forces applied to the end effector elements after they have been in a closed configuration for a time period T. Overgripping causes strain on the instrument, in particular stretching of the driving elements. By reducing the time during which the instrument is in the overgripping configuration, the methods described herein aid to reduce the ageing of the instrument.

The illustrated steps of the flow charts of FIGS. 4 and 5 are just those steps relevant to the problem addressed herein. The control system performs many other steps during the control loops shown in FIGS. 4 and 5. Those other steps are not shown in FIGS. 4 and 5.

FIGS. 6 and 7 are not to scale.

The end effector may take any suitable form. For example, the end effector could be a pair of curved scissors, an electrosurgical instrument such as a pair of monopolar scissors, a needle driver, a pair of jaws, or a fenestrated grasper.

The robot described herein could be for purposes other than surgery. For example, the port could be an inspection port in a manufactured article such as a car engine and the robot could control a viewing tool for viewing inside the engine.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A control system configured to control manipulation of a surgical instrument in response to manipulation of a remote surgeon input device, the surgical instrument comprising opposable first and second end effector elements connected to a shaft by an articulated coupling, the articulated coupling comprising a first joint driveable by a first pair of driving elements so as to permit the first end effector element to rotate, and a second joint driveable by a second pair of driving elements so as to permit the second end effector element to rotate, the control system configured to:
   detect a change of configuration of the surgeon input device to a gripping configuration at time t;
   respond to the change of configuration of the surgeon input device to the gripping configuration by commanding gripping forces to be applied to the first and second pairs of driving elements, so as to cause the first and second end effector elements to rotate in opposing rotational directions towards each other with a gripping closing force to an overgripping closed configuration;
   detect if the first and second end effector elements are still in any overgripping closed configuration at time t+T, wherein T is dependent on instrument type such that T is different for different instrument types; and
   if it is detected that the first and second end effector elements are still in any overgripping closed configuration at time t+T, command a reduction in the force applied to the first and second pairs of driving elements, thereby causing the first and second end effector elements to subsequently be held in a further closed configuration with a reduced closing force.

2. A control system as claimed in claim 1, configured to command the reduction in force to be applied gradually over a time ΔT.

3. A control system as claimed in claim 1, configured to:
   detect a command from the surgeon input device to disengage active control of the surgical instrument by the surgeon input device; and
   in response to the detected command:
      disengage active control of the surgical instrument by the surgeon input device, and
      maintain the first and second end effector elements of the surgical instrument in the further closed configuration with the reduced closing force.

4. A control system as claimed in claim 3, configured to:
   detect a command at time T' from a surgeon input device to engage active control of the surgical instrument by the surgeon input device; and
   in response to the detected command:
      engage active control of the surgical instrument by the surgeon input device, and command gripping forces to be applied to the first and second pairs of driving elements, so as to cause the first and second end effector elements to be forced in opposing rotational directions towards each other with a gripping closing force.

5. A control system as claimed in claim 4, wherein the command detected at time T' is from the same surgeon input device that disengaged active control of the surgical instrument and engaged active control of the further surgical instrument.

6. A control system as claimed in claim 4, wherein the command detected at time T' is from a different surgeon input device to the surgeon input device that disengaged active control of the surgical instrument and engaged active control of the further surgical instrument.

7. A control system as claimed in claim 4, configured to command forces to be applied to the first and second pairs of driving elements instantaneously.

8. A control system as claimed in claim 7, wherein 1 second<T<10 seconds.

9. A control system as claimed in claim 8, wherein 30 seconds<T<3 minutes.

10. A control system as claimed in claim 9, wherein the gripping configuration of the surgeon input device comprises a rotational position of the trigger relative to the body that is within a specified range of rotational positions.

11. A control system as claimed in claim 9, wherein gripping configuration of the surgeon input device comprises a linear position of the trigger relative to the body that is within a specified range of linear positions.

12. A control system as claimed in claim 4, configured to command the forces to be applied to the first and second pairs of driving elements gradually over a time ΔT'.

13. A control system as claimed in claim 1, configured to, on detecting activity of the surgeon input device at time T', command gripping forces to be applied to the first and second pairs of driving elements, so as to cause the first and second end effector elements to be forced in opposing rotational directions towards each other with a gripping closing force.

14. A control system as claimed in claim 13, wherein the detected activity of the surgeon input device at time T' is a movement of the user indicative of the user's presence or focus of attention on the surgical instrument.

15. A control system as claimed in claim 13, wherein the detected activity of the surgeon input device at time T' is one of: a rotation or translation of the surgeon input device in its workspace, a detection of a user's hand in contact with the surgeon input device, or an actuation of an input on the surgeon input device.

16. A control system as claimed in claim 1, wherein the surgeon input device comprises a body and a trigger, and the surgeon input device is in a gripping configuration when the trigger has a position relative to the body that is within a specified range.

17. A control system as claimed in claim 1, configured to command gripping forces to be applied to the first and second pairs of driving elements by:
  applying a first gripping force to a first driving element of the first pair of driving elements, and
  applying a second gripping force to a second driving element of the second pair of driving elements,
  wherein the magnitudes of the first and second gripping forces are the same.

18. A control system as claimed in claim 1, configured to command a reduction in the force applied to the first and second pairs of driving elements by a function dependent on instrument type.

19. A control system as claimed in claim 1, wherein the gripping forces are maximum forces.

20. A control system as claimed in claim 1, configured to continue to detect the gripping configuration of the surgeon input device for the time T.

21. A control system as claimed in claim 1, wherein the time T is dependent on one or more of: a type of surgical operation being performed; a stage of the surgical operation; a total running time of the first and second pairs of driving elements; a total overgripping time, optionally weighted by the force applied to the first and second pairs of driving elements; whether the surgical instrument is engaged or disengaged from the surgeon input device; risk factors specific to the surgical operation; an operation mode of the control system; and a temperature of joints of a robot arm holding the surgical instrument.

* * * * *